United States Patent [19]

Elahi

[11] 4,131,544
[45] Dec. 26, 1978

[54] MACROENCAPSULATED SORBENT ELEMENT AND PROCESS FOR USING THE SAME

[76] Inventor: Nasik Elahi, 41-77 Frame Pl., Flushing, N.Y. 11355

[21] Appl. No.: 711,293

[22] Filed: Aug. 3, 1976

[51] Int. Cl.$^2$ .................. B01D 15/00; B01D 53/02
[52] U.S. Cl. .................... 210/40; 23/230 B; 55/387; 422/69; 422/88; 210/282; 23/232 R; 210/502; 210/DIG. 23; 210/DIG. 24
[58] Field of Search ............ 23/230 B, 232 R, 254 R, 23/259; 55/387, 40, 282; 210/502, 504, DIG. 23, DIG. 24

[56] References Cited

U.S. PATENT DOCUMENTS

| | | | |
|---|---|---|---|
| 3,252,270 | 5/1966 | Pall et al. | 210/502 UX |
| 3,310,176 | 3/1967 | Ziherl et al. | 210/282 X |
| 3,327,859 | 6/1967 | Pall | 210/502 UX |
| 3,507,618 | 4/1970 | Murty | 23/230 B |
| 3,519,390 | 7/1970 | Dickey et al. | 23/230 B |
| 3,743,482 | 7/1973 | Eisentrant | 23/230 B |
| 3,888,250 | 6/1975 | Hill | 210/502 X |

Primary Examiner—Frank A. Spear, Jr.
Assistant Examiner—Richard W. Burks
Attorney, Agent, or Firm—Kenyon & Kenyon Reilly Carr & Chapin

[57] ABSTRACT

Described herein is a sorbent element, especially useful for removing matter from a liquid system, comprising particulate sorbent material such as charcoal, ion exchange resins and silicas, substantially loosely encapsulated within a porous filter membrane such as woven polypropylene or Teflon. A particular application of the encapsulated element is in the qualitative and quantitative analysis of drugs contained in biological samples. Sorption processes utilizing the novel sorbent element are also described, as well as apparatus for performing analytical techniques utilizing the sorbent element.

14 Claims, No Drawings

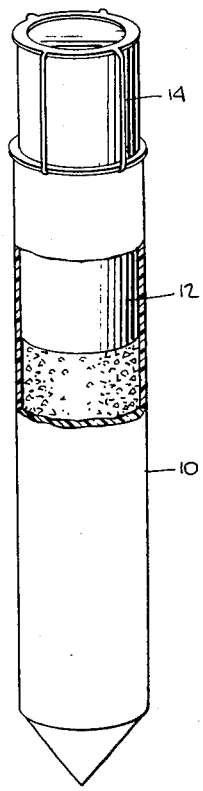

MACROENCAPSULATED SORBENT ELEMENT AND PROCESS FOR USING THE SAME

BACKGROUND OF THE INVENTION

This invention relates to the removal of one or more materials from a medium, and more particularly, to a sorption method and element for effecting such removal.

The prior art has long been aware of, and has utilized, the sorbent properties of certain materials to effect the removal of matter from a liquid or gaseous medium. The myriad uses of such sorbent materials include such divergent processes as the removal of undesirable impurities from a liquid system and the removal of a desired solid specie or species from a liquid system containing that specie in a dissolved or dispersed state. Typical sorbent materials include charcoal and ion-exchange resins which display a marked affinity for a wide variety of dissolved or dispersed solids.

Such sorbent materials have been utilized in various analytical techniques where it is desired to quantitatively remove one or more solid materials from liquid system. A specific example of such utilization lies in the field of drug analysis, i.e., the analysis of a biological fluid system such as blood or urine to determine both the type and quantity of whatever drugs may be contained therein. In such methods, urine, for example, is passed through or otherwise contacted with a sorbent material capable of removing certain drugs from the liquid system. The sorbent is then processed in a series of washings to result in an effluent of the removed drug or drugs. This effluent is then analyzed, for example by chromatographic techniques, to determine the type and quantitative amount of drugs contained in the system.

Additional examples of such analytical techniques include the determination of the quantity and type of pollutants in air samples.

As is apparent from the foregoing description, these analytical techniques, to be effective, require a near quantitative removal of the solid matter from the liquid or gaseous system, as well as the eventual near quantitative removal of the solid matter from the sorbent material. Such requirements have proven to be exceptionally difficult to meet and, indeed, are often counter-productive. For example, it is generally found that finely-divided sorbents, due to the attendant exposure of a large surface area, more effectively sorb solid matter from liquid systems. Yet this same desirable attribute significantly hampers the ability to quantitatively remove the solid matter, since the finely divided sorbent often disperses into and is carried away with the liquid system or contaminates the desired effluent containing the solid matter. In the specific example of drug analysis, the presence of any such sorbent material in the drug solution subjected to chromatographic analysis results in possible incorrect quantitative readings and "background" interference with the time and size of the peaks associated with the particular drug.

Accordingly, many prior art techniques for enhancing the effectiveness of sorptive materials are not applicable to analytical techniques designed to quantitatively recover matter removed by the sorbent.

It is an object of this invention to provide a process for the quantitative sorption of matter from a liquid or gaseous system.

Another object of this invention is to provide a process for the quantitative sorption of solid matter from a liquid system and the subsequent quantitative removal of the solid matter from the sorbent material.

Yet another object of this invention is the provision of a sorbent material capable of quantitatively sorbing solid matter from a liquid system and of quantitatively yielding such sorbed solid matter.

A more specific object of this invention is the provision of a process and sorptive element for the quantitative analysis of durgs contained in a biological liquid system.

Another object of this invention is the provision of a process for removing gaseous matter from a liquid system.

A further object of this invention is the provision of a process for removing solid matter from a gaseous medium.

An additional object of this invention is to provide an apparatus useful in the sorption of solid material from small liquid samples.

SUMMARY OF THE INVENTION

These and other objects are attained by a process which comprises the removal of matter from a liquid or gaseous system utilizing a sorbent material which is substantially loosely encapsulated in a porous filter membrane.

In accordance with this invention, the sorbent material may be any of the large number of such materials known to the art such as charcoal, aluminas, siliceous materials such as silica gels, diatomaceous earth and the like, cationic or anionic ion exchange resins, ligand exchange resins or any mixture of one or more of these sorbent materials. The sorbent material is preferably in particulate form and of a sufficiently small particle size to expose the largest possible surface area and active sorption sites.

The encapsulating material for use in this invention comprises a porous filter membrane fashioned from any of a large number of commercially available materials such as polypropylene, Teflon and the like. The sorbent material is encapsulated within the porous filter membrane in such a manner as to permit the sorbent to agitate freely within the encapsulated system and hence is to be distinguished from a coating on the sorbent particles. Additionally, since the sorbent is contained within an encapsulating membrane it is to be distinguished from those prior art techniques utilizing a matrix consisting of exposed sorbent material and polymeric material. In order to prevent collapse of the encapsulating material about the sorbent, it is necessary to provide the encapsulating material either in the form of a rigid structure or to utilize a skeletal support structure in conjunction with the membrane.

As will be described hereinafter in more detail, the porosity or pore size of the encapsulating material and its relation to the particle size of the sorbent material must meet certain requirements in order to function effectively in accordance with this invention.

In a specific embodiment of this invention, the sorbent material is provided in the form of a cartridge or capsule comprising a predetermined quantity of particulate sorbent material loosely enveloped within an encapsulating membrane. These capsules or cartridges may then be utilized for the sorption of solid matter from liquid or gaseous systems as will be described in detail hereinafter.

In a preferred embodiment of this invention, the sorption of solid matter from a liquid medium using the encapsulated sorptive material as earlier described is accompanied by the application of a positive pressure and agitation to the mixture of liquid medium and encapsulated sorbent. Among the many advantages of the encapsulated sorbent of this invention is that such an application of pressure and agitation, which increases the sorption efficiency of the sorbent, does not at the same time tend to compact the particulate sorbent since the encapsulating membrane protects the sorbent contained within.

The process and sorbent element of this invention possess a number of advantages heretofore unattained by prior art techniques. Thus, in prior art methods wherein a liquid medium is directly contacted with a finely-divided sorbent, such as in a columnar arrangement, the contact, particularly at high throughputs, generally results in a substantial compaction of the particulate sorbent. The result of this compaction is generally to plug the column and therefore reduce the efficiency of contact. In processes such as the earlier described drug analysis process, involving a considerable number of elutions before obtaining the desired sample for analysis, this compaction of the sorbent particles is particularly aggravated. In accordance with this invention, the encapsulating membrane serves both to resist this adverse effect of liquid contact on the sorbent.

Further, those prior art techniques wherein finely-divided sorbent is directly admixed with the liquid medium and agitated therewith to effect the desired contact, result in breaking up of the sorbent and the attendant possibility of such particles contaminating the liquid system, leading to quantitative losses etc. Complete separation of such finely-divided contaminant sorbent from a liquid system is extremely difficult. Again, in the earlier-described drug analysis process, the repeated number of elutions with various solvents, makes this in-process sub-division of the sorbent acutely detrimental. The encapsulating membrane of the present invention serves both to prevent the formation of sorbent fines and, if formed, to restrain such fines from entering the liquid phase.

Additional advantages of the present invention include the ability to prepare discrete capsules containing a pre-determined quantity of sorbent enveloped within an encapsulating membrane, which capsules may be prepared in any desired shape suited for the particular processing needs. These capsules or cartridge-like sorbents greatly facilitate solid matter removal in analytical processes. For example, one or more of the capsules may simply be dropped into a vial containing the particular liquid system and the vial then agitated under positive pressure to effect excellent contact of sorbent material with the liquid system.

In accordance with this invention, there is also provided an apparatus for conducting analytical techniques utilizing the sorbent element and process of the present invention. The apparatus comprises means for receiving a system of liquid sample and encapsulated sorbent element, means for closing said system to the atmosphere, means for applying a positive pressure to the sample, and means for retaining the applied pressure at a substantially constant value.

In accordance with this invention, "sorption" is intended to broadly describe the removal of a matter from a liquid or gaseous system based on the attraction, physical or otherwise, of the matter to a material hereinafter referred to as a "sorbent material." As is well-known in the art, such sorption processes may involve adsorption and/or absorption as well as other, less easily categorized attractive forces.

According to this invention, "encapsulated sorbent element" is intended to refer to the overall combination of sorbent material and porous encapsulating membrane material, i.e., sorbent material substantially loosely encapsulated within a porous encapsulating membrane. Thus, where reference is made to the void volume "within the encapsulated element," it is intended to describe the void space existing between the particulate sorbent material and the outer encapsulating layer.

Reference to "quantitative removal" of matter from a liquid or gaseous system will be recognized by the art as necessarily relative to some degree and is intended merely to reflect a greater degree of removal than generally achievable in the art.

As will become apparent from the more detailed description and examples which follow, the sorbent element and process of this invention has applicability in a wide variety of technological areas. Such uses include the sorption of solid matter from liquid or gaseous systems and the sorption of gaseous matter from a liquid system.

DETAILED DESCRIPTION OF THE INVENTION

Figure 1:
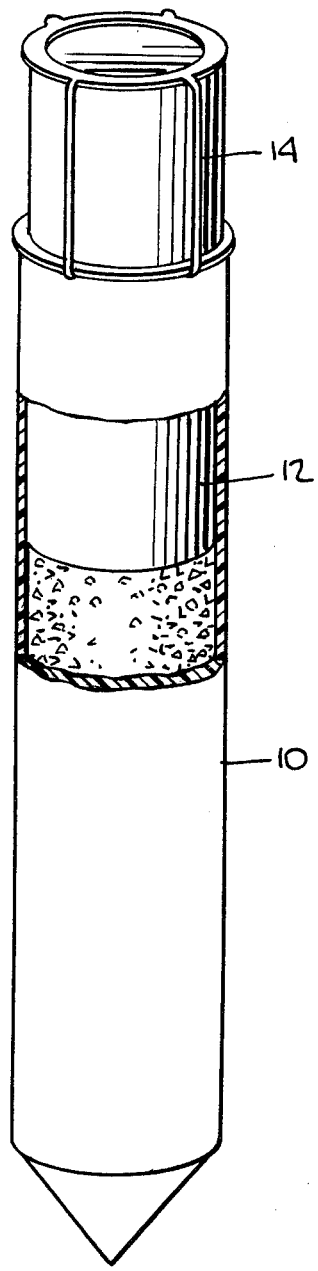
FIGS. 1, 2 and 3 are diagrammatic representations of three embodiments of the invention showing, respectively, clamping, locking and threaded means for holding a plunger in position in the receptacle of the invention.

As earlier described, the porous encapsulating filter membrane may be prepared from polymeric materials such as polypropylene, Teflon, cellulose acetates as well as either woven or naturally derived fibrous materials. In order to prevent the collapse of the encapsulating material about the sorbent particles, i.e., in order to maintain a suitable void volume within the encapsulated element it is necessary that the encapsulating membrane possess a certain degree of rigidity. Such rigidity may be provided by the encapsulating membrane material itself, or, where the encapsulating material is inherently flexible, by a suitable rigid skeletal support structure such as wire or rigid polymeric or resinous material such as Teflon.

The preparation of the encapsulated sorbent element involves simply the provision of a desired quantity of particulate sorbent in a material which may be molded and sealed to form a substantially enclosed structure. As the nature of the preferred encapsulating materials are polymeric or resinous, heat sealing has proven to be effective means for enclosing the encapsulating material about the sorbent particles.

With reference to the encapsulated element, the volume of the overall element itself is preferably at least about 25% greater than the volume of the particulate sorbent contained therein. The provision of this void volume enables the particulate sorbent to move freely within the capsule and thereby continuously expose fresh active sorption sites to the liquid system. Additionally, where ion exchange resinous particles are utilized as the sorbent material, the attainment of the above-referred to void volume should take into account the swelling properties of the particular resin and accordingly may require that a larger void volume exist at the initial preparation of the sorbent element.

Of necessity, the encapsulating membrane material must possess a porosity which will permit the liquid medium to come in contact with the encapsulated sorbent particles. Another significant advantage of this invention is that the pore size of the encapsulating material may be utilized to selectively "screen" large molecules from the sorbent particles, i.e., to serve as a filter medium for undesired particles. In this manner the sorbent more efficiently sorbs the desired particles from the liquid system and the possibility of large molecules blocking or shielding the active sorbent sites is greatly diminished. In order to prevent these larger molecules from blocking the pores of the encapsulating material, and hence reducing the contact between sorbent and liquid or gas, it is generally preferred to either continuously or periodically agitate the encapsulated element within the liquid or gaseous system.

Based upon the foregoing considerations, it may be seen that the pore size of the encapsulating membrane may vary widely depending upon a variety of factors. Thus, the pores must be smaller than the size of the particulate sorbent encapsulated therein to prevent the sorbent from escaping therefrom and entering the liquid system. At the same time, the pore size of the encapsulating material must not be so small as to prevent contact between the solid matter desired to be removed from the liquid system and the sorbent. In general, for most analytical techniques, the particle size of the desired solid matter is expected to fall within a given range. Hence, the pore size of the encapsulating material can be made or chosen to permit passage of the largest sized desired particles expected. Undesired larger molecules will then be screened by the encapsulating membrane.

As earlier noted, the application of a positive pressure has been found beneficial in achieving the desired quantitative sorption of solid matter from the liquid system. Utilizing one or more encapsulated elements in accordance with this invention, this pressure may be conveniently applied in the form of a plunger-like device, e.g., a closed vessel not unlike a hypodermic syringe, but modified in that the walls are generally thicker than those utilized in conventional syringes. Thus, liquid sample together with one or more encapsulated sorbent elements are introduced into the body of the syringe and the plunger mechanically depressed to apply pressure to the system. The pressure can be constantly applied either by continuously holding the plunger in place or by locking means designed to retain the plunger in its depressed state. Somewhat more sophisticated pressure devices are commercially available such as the stirred cells manufactured by Amicon Corporation under the trade designation of Models 12, 52, 202 and 402.

Thus, as shown in FIG. 1, the apparatus for use with the sorption element and process of this invention comprises hollow cylindrical receiving means 10 to which is added the sorbent element along with liquid sample from which solid matter is to be removed. The receiving means is closed at its lower end and a positive pressure is applied by depression of plunger 12 which is designed so as to form a substantially leak-proof seal with the cylindrical receptacle. The plunger is then locked in place to maintain the pressure at a constant value by clamping means 14 which may comprise any suitably shaped metal or wire. The thus clamped cylinder may then be agitated either by hand or mechanically.

Figure 2:
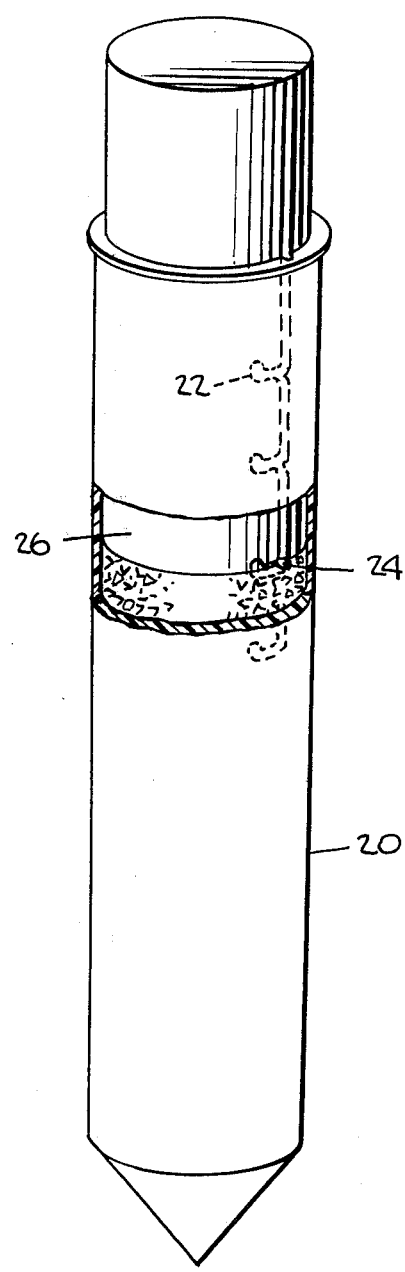

FIG. 2 represents a modified version of the syringe-like sorption vessel comprising hollow cylindrical receiving means 20 having one or more locking means 22 on the inner wall thereof. Locking means 22 are adpated to receive tab means 24 located on plunger 26 and thus maintain the plunger in a constant position. In operation, the plunger is depressed to the desired level and then rotated to engage locking means 22.

In either apparatus as above described, the lower portion of the vessel may be closed to atmosphere either by suitable fabrication or by the provision of a stopcock or other device.

Figure 3:
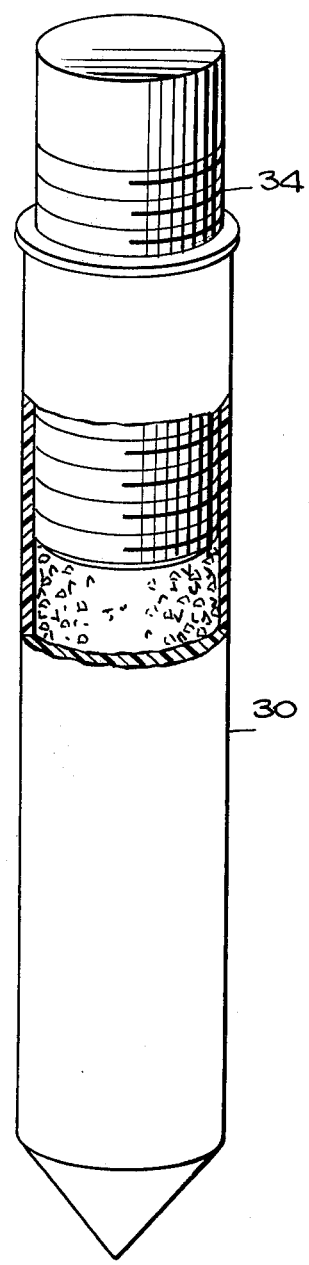

In an alternative embodiment shown in FIG. 3, plunger means 34 is screw-threaded and adapted to engage the threading provided in cylindrical receptacle means 30.

The following examples are provided to illustrate the features of the present invention and the many uses therefor.

EXAMPLE I

In this example, acid or neutral drugs are sorbed from blood to determine the type and quantity of the drugs within the bloodstream.

250 milligrams of charcoal granules (Neutral Pharmaceutical Grade available from American Norite) having a particle size ranging from about 12 to 30 mesh (U.S. Sieve series) are placed within a woven polypropylene sheet having an average pore size of 70 to 100 microns. A teflon skeletal support is provided in the form of heat-fused perpendicular circular rings around which the polypropylene sheet is formed and heat sealed. The void volume within the encapsulated element is approximately 30%.

To one ml. of blood is added 0.5 cc of pH 11.0 buffer and then diluted with one ml. distilled water in the barrel of a modified hypodermic syringe whose tip has been closed to the atmosphere. The previously described capsule is then added to the blood system and the syringe put under pressure by mechanical depression of the plunger. The plunger is maintained in this state by virtue of a latching device provided within the syringe barrel, as shown in FIG. 2.

The contents of the pressurized device are agitated by hand for approximately 10-15 minutes at which point the fluid contents are removed therefrom. The sorbent capsule is then washed with distilled water (under pressure and with agitation) in three successive washings. After removal of the liquid contents, the capsule is then contacted in the syringe with ether in three successive one ml. extractions, again under pressure and with agitation. The liquid fractions resulting therefrom are evaporated to dryness and subjected to chromatographic analysis.

The foregoing procedure is equally applicable to the extraction of basic drugs (e.g., amphetamines, alkaloids) with the provision that the original blood sample be buffered to a pH of 11.0 and that the final extractions be conducted with acidified methanol or mixture of chloroform and isopropanol.

Acid, neutral and basic drugs may be simultaneously removed from a blood sample utilizing the foregoing technique modified in that the elution after the washing with distilled water is with a mixture of ether/chloroform/isopropanol (5:5:1 volume).

Similar methods may be utilized where urine is the fluid to be analyzed.

EXAMPLE II

In this example, acidic, basic and neutral drugs are recovered from tissue specimens.

The capsule described in Example I is utilized in this embodiment with the modification that it contains a greater amount of the sorbent medium, 500 milligrams.

The procedure is as follows:

Five grams of tissue are thoroughly homogenized in a mixer. The tissue is then hydrolyzed with 5–10 ml. of 0.45N-sodium hydroxide solution, for at least fifteen minutes. The contents are centrifuged and the aqueous layer collected in a separate vessel. This step allows both the bound and the unbound acidic and some acidic drugs to pass into the alkaline solution.

The same tissue sample is next hydrolyzed with 0.5–N hydrochloric acid and the hydrolysate collected in the above manner. The combined aliquot of the hydrolysates contains the acid, basic and neutral drugs in the aqueous phase.

The combined aqueous phase is adjusted to a pH of 7. To this is then added 2 ml. of pH 11 carbonate-bicarbonate buffer, and mixed. The contents are placed in a positive pressue device, the capsule added and the contents shaken for five minutes under pressure. The capsule is retrieved, washed with distilled water and the sorbed drugs eluted by using an appropriate solvent system. It must be pointed out that the hydrolysis procedure outlined can be varied as to the type, and strength of the hydrolyzing solution used. The only mandated step is the addition of sufficient amount of carbonate-bicarbonate ions in the sample aliquot. Prior art studies have shown the presence of these ions as enhancing the sorbent properties of charcoal.

The elution of the drugs from the sorbent element can be general as well as specific. Use of solvent systems like ether-chloroform-isopropanol (5:5:1 v/v) is a general system permitting the desorption of all types of drug categories. Ether used alone would primarily elute acidic drugs, whereas chloroform-isopropanol (5:1 v/v) would desorb basic and neutral compounds. Still other solvent systems can be affected to yield the desired selectivity.

EXAMPLE III

In this example, a macro encapsulated ion-exchange sorbent is used for the rapid group separation of simple biological mixtures.

Appropriate ion exchange resins (Bio-rad, Sephadex products) are selected, depending upon the particular application. The encapsulating membrane is polypropylene, woven, with adequate skeletal support. The volume of the membrane is 20–30% greater than the volume of the swollen sorbent. A positive pressure device with agitation is also required.

The various applications of this material can be illustrated by the group separation of nucleosides from nucleotides following the method of Deutscher, N. (j. Biol. Chem., 247, 469 (1972)).

The encapsulated ion exchanger (1-X8) was hydrated with deionized water, thoroughly washed under positive pressure and equilibrated with a buffer solution. An RNA hydrolysate was adjusted to pH 4–5 and the capsule added to it. The contents were shaken under positive pressure and quickly drained. The nucleosides were eluted from the sorbent element with water. Elution with 0.05N HCl yielded the nucleotides.

A range of other biological mixtures can be treated in a similar manner to effect group separations.

EXAMPLE IV

This example described the macro encapsulation of affinity sorbents for the isolation of proteins fractions, nucleic acids glycoproteins, polysaccharides and other classes of naturally occurring compounds.

Affinity chromatography utilizes the specificity of biological interactions. The sorbent e.g., Sepharose products, are prepared by covalently binding and appropriate binding ligand to an insoluble matrix. The binding ligand can then absorb from solution the specific biological component to be isolated, without affecting the specific binding activity of the biological component. After the unbound substances have been thoroughly washed away, the bound component is desorbed.

The macro encapsulation technique offers an improvement over the existing techniques.

An appropriate affinity product [(depending upon the biological component to be separated) e.g., CNBr-activated Sepharose 4B, AH-Sepharose 4B, CH-Sepharose 4B, Epoxy Activated Sepharose 6B, or Activated CH-Sepharose 4B] is selected. The required amount, say 1 gram of the freeze-dried material is selected. Because of the swelling properties of the affinity sorbents, the encapsulating medium; polypropylene, teflon etc. has to have a volume at least 5 times the dried sorbent. The shape of the encapsulated product can be flat disc with the sorbent material sandwiched in, or rounded or oval, in which case it may require a skeletal support.

The encapsulated freeze-dried matrix is prepared for use according to the affinity material selected.

A coupling procedure for using a CNBr-activated Sepharose 4B, serves as a specific example.

The freeze dried encapsulated matrix is placed in a positive pressure and agitation device and washed with 1mM HCl (about 200 ml for every gram weight). This step swells the material into a gel approximately four times the freeze dried volume.

The protein sample to be used is dissolved in a NaHCO$_3$ buffer (0.1M, pH 8.3) containing 0.5M NaCl.

The protein solution is placed in the positive pressure and non-magnetic agitation device containing the treated encapsulated affinity gel, and allowed to mix overnight at 4° C.

The excess protein is washed away and the remaining active groups are blocked by using an appropriate coupling buffer followed by washing with ethanolamine solution for at least two hours at room temperature, using positive pressure and agitation.

After appropriate washings, desorption is accomplished usually by an increase in ionic strength or a shift in pH. More specific methods can be employed for elution.

Each of the steps requires a positive pressure device that has the feature of a non-magnetic agitation. This is usually provided in the agitation cells commercially available for ultrafiltration. The only adaptation needed in the commercially available models is to replace the filter membrane of the cell with a rigid non-porous membrane that can withstand pressure. This allows the pressure to build up in the cell.

Another form of the positive pressure device is the modified syringe described earlier in FIG. 2. The barrel is locked into position to provide the appropriate pressure. Agitation of the solution is accomplished by a manual rotater.

EXAMPLE V

This example describes the application of the macro-encapsulated solvent for detection of minute quantities of Synthetic dyestuffs in juices and wine.

The encapsulated sorbent is polyamide (0.5 grams) and a polypropylene filter membrane is formulated to make disc shaped capsules of diameters to fit commercially available ultrafiltration filter holders e.g., Millipore Swinny holders: 13 to 25 mm. dia.)

The technique for isolation and purification of the synthetic dyestuffs is as outlined by G. Lehmann, et al., (Z. Lebensmittel 143, 191, (1970)) whereby acid dyestuffs are sorbed on polyamide and natural dyestuffs and plant constituents excluded.

100 ml of sample are added to 5 ml of formic acid in methanol (40 ml, formic acid + 60 ml. methanol). The contents are placed in a hypodermic syringe attached to a Swinny holder containing encapsulated polamide. The filtrate is discarded.

To clean up the sorbate of residual anthocyanes, 4 repeated washes, 5 ml. each, of formic acid-methanol solution are made.

The encapsulated sorbent is then washed with approximately 60 ml. of distilled water until the wash shows the pH value of the distilled water.

The sorbent is then eluted with 2 washes, 3 ml. each of methanol-ammonia solution (5 ml. conc. ammonia + 95 ml. methanol). Elution is completed by adding 3 ml. of methanol. The ammoniacal eluate is acidified with 5 ml. of formic-acid-methanol solution. Final volume is made to 15 ml. with distilled water.

The eluate received at the end contains the synthetic dyestuffs ready to be chromatographically identified.

EXAMPLE VI

In this example is described the purification of organic solvents for optical applications.

In many laboratory instrumentation applications e.g., spectroscopy, ultra-pure spectral grade solvents are needed. These are usually available commercially but once these bottles are opened impurities can easily set in. It is advisable to undertake a purification just prior to use, to prevent such contaminations.

For smaller laboratory applications the encapsulated sorbents (e.g., basic alumina, neutral alumina, alumina acid, silica gel etc.) either alone or in mixtures prepared as diskets can be extremely helpful.

A specific example for the removal of peroxides in ether is as follows:

(1) The sorbent (alumina) is encapsulated in an inert jacket (e.g., Teflon) in a disc shape and sealed either at the edges or a grid seal running throughout the surface to prevent clumping of the sorbent;

(2) The discs are made to size so they completely set into commercially available holders for ultrafiltration membranes;

(3) Attached to the membrane holder is a glass syringe. It offers sufficient positive pressure to propel the solvent through the capsulated sorbent disc. The sample collected would be free of impurities and ready to use;

(4) The disc can be readily retrieved and replaced by yet another.

The flow rates can be readily adjusted by regulating the manual pressure on the syringe.

EXAMPLE VII

This example describes the application of macro-encapsulated sorbent technique for bound an unbound drug studies.

The encapsulated sorbent is neutral, pharmaceutical grade charcoal in woven polypropylene encapsulant. Other sorbents e.g., florisil, XAD-2 resin, ionic SA-2 etc. can also be substituted.

Drug binding studies are becoming a reliable tool for determining the optimum therapeutic dosage for patients, on an individual basis. This stems from the findings of recent studies. It has been found that the drugs administered to humans equilibrate in the blood both in the free state and bound to the larger protein molecules. Of this only the unbound drug part is biologically active. The bound drug is rendered pharmacologically inactive. The level of binding is found to be on an individual basis and hence the need for the determinations.

The procedure can be performed in one of two ways: a) a sample of blood is taken and incubated with a known amount of drug for and appropriate length of time or b) the patient is given an experimental dosage and a blood sample or samples taken, after the appropriate length of time, depending upon the drug administered.

The sample is processed using the macro-encapsulation technique. The capsule is added to the blood sample under positive pressure, and shaken for about 15 minutes. The sorbent adsorbs the unbound drug or drugs in the blood. The capsule is washed three times with distilled water and eluted with a suitable solvent and then quantitatively analyzed by various instrumentation techniques.

The blood containing the bound drug only is then subjected to mild hydrolysis. This releases the drug from its macromolecular base. The same recovery procedure is used with a fresh capsule, the drug recovered and quantitated.

The procedure allows a rapid determination of both the bound and unbound drug levels.

EXAMPLE VIII

This example describes the use of an encapsulated sorbent to trap volatile fractions from biological fluids and other extracted gas chromatographic fractions for mass spectrometric analysis.

The latest advance in instrumentation technique in analytical chemistry is using mass spectrometry in conjunction with gas chromatography. However, the on-line sampling appraoch has been shown to have several disadvantages. Amy and other investigators have demonstrated the advantage of trapping individual components on a suitable sorbent, e.g., charcoal and subsequently releasing the components into the ion source of the spectrometer.

The encapsulated sorbent technique offers a means of further making the entire procedure simple and rapid.

The capsules are prepared by sealing appropriate amounts of activated (50, 100, 150 mgs.) cocoanut charcoal, 70-100 mesh, (or other mesh sizes), the Teflon TFE filter membranes commercially available from Amicon, Millipore, Gellman etc.

The capsule is placed in a special holder. The device has two pieces, a screw-thread base that screws onto the rest of the device, giving a gas-tight union. The rest of the device has a nozzle end of sufficient length. At the tip of the nozzle is an on-off let valve. The material of construction is Teflon. This material can withstand high temperature and is quite inert, thus eliminating interference in the ultra-sensitive instruments.

The nozzle end fits into the effluent end of the gas chromatograph column. The opening has an inert rubber or Teflon nipple to make a tight seal around any sized effluent end.

The capsule is placed inside the device and screwed tightly. The device is then heated to eliminate any residuals on the sorbent surface and the compartment is flushed with nitrogen or an appropriate inert gas.

The treated charcoal is then ready. The nozzle end is fitted on the effluent end, the on-off valve is turned on and the chromatographic fraction is pumped in. The valve is shut and the device containing the chromatographic fraction is sorbed.

The sorbed fraction is then connected to the ion source of the mass spectrometer and can be readily eluted by appropriate heating.

In much the same way, the same arrangement can be used to sorb volatile components, gases etc. from biological matrix. These can be subsequently further purified by passing through gas chromatographic columns, the individual components sorbed and then fed into the mass spectrometer.

The less volatile fractions can be extracted by means of organic solvents, resolved in the gas chromatograph and then sorbed for mass spectrometer runs.

EXAMPLE IX

This example outlines the use of an encapsulated sorbent element for the determination of drug levels in biological specimens by using the Radio-immuno Assay (RIA) technique.

Drug determination by the RIA technique offers some unique features. The foremost of these is specificity. The technique utilizes antibodies developed specifically to a drug moiety. The antibodies would interact only with the specific drug and no other class of compounds. These antibodies have been commercially developed. For use in RIA determinations, they are commercially available already bound to radio-labelled drugs. This antibody-radiolabelled-drug complex is analyzed to determine the level of radioactivity, and serves as the reference for the subsequent determination of the drug concentration in the unknown biological specimen.

To determine the concentration of a drug in a biological specimen, known aliquots of the commercially available antibody drug (labelled) complex are added to the sample. A competitive displacement takes place, by virtue of which the unlabelled drug in the biological sample displaces an equal amount of the labelled drug from its antibody-drug (labelled) complex. The radiolabelled drug thus freed is separated from the sample and the remaining radioactivity levels are determined, using either a gamma counter or a scintillation counter. The loss in radio-activity is a direct extrapolation of the drug concentration in the biological sample. The use of an encapsulated sorbent offers an efficient and rapid means of affecting the separation of the freed radioactive drug from the specimen pool, prior to reading the remaining radioactivity level in the Gamma or Scintillation counters.

A specific example for the determination of digoxin levels in human serum is offered as an illustration:

The capsules are prepared as follows: 100 milligrams of Neutral, Special Grade charcoal is encapsulated in teflon or polypropylene. The standards for rigidity of skeleton, void volume and porosity of the encapsulating medium described earlier are all applied as required. The capsules are then pretreated in a 250 milligram percent solution of Dextran T70 (Pharmacia Co.) in a pH 7.4 phosphate buffer, under positive pressure and stirred overnight. The capsules are then retrieved and allowed to air dry.

At the time of analysis, the dextran-coated encapsulated sorbent is suspended in a sufficient amount of pH 7.4 phosphate buffer. It can be stored for two weeks in this state.

Utilizing a threaded tube as shown in FIG. 3, 0.2 ml. of human serum is pipetted into the threaded tube. To this is added 0.8 ml. of Phosphate buffered saline and 0.01 ml of Tritium labelled (3 Ci/5 ml. of solution) digoxin. To this is then added 0.01 ml. of the Anti-Digoxin serum or antibody. The screw top is placed and the contents vigorously shaken on a vortex agitator. Displacement takes place whereby the labelled drug from the antibody-drug complex is replaced by the unlabelled drug in the sample. The contents are next transferred to a pressurized device and a pretreated capsule added. The contents are pressurized and agitated for five minutes. The capsule is retrieved and discarded. The fluid contents are transferred to a scintillation vial and the remaining radioactivity determined in a scintillation or gamma counter.

EXAMPLE X

In this example, application is made of the macro-encapsulated sorbent in hemodialysis, hemoperfusion and peritoneal dialysis.

Yatzidis was the first investigator to point out the benefit of using carbon hemoperfusion for overdose cases. The spproach offers the most efficient way of cleansing the blood stream of the toxic drugs and hence avoid overdose death.

However, several workers have pointed out the deleterious impact of untreated carbon granules. The granules have a tendency of leaving ultrafine dust which can penetrate the semipermeable membranes used in the artificial kidney-type apparatus. This can cause excessive blood cell damage and the phenomenon of carbon micro-emoblization.

The approach suggested is to thoroughly clean the charcoal granules of residual "fines" and coat them with a biocompatible acrylic hydorgel polymer 2 to 4%, prior to use.

The macro-encapsulated sorbent technique of the present invention affords a further refinement to the approach. The refined, polymer-coated carbon is encapsulated in sheets of the appropriate cellulose semipermeable membrane with inter-spaced grid seals to hold the sorbent in place. The dimensions of the sheets can be made to adapt to the shape requirements of the various types of hemodialysis apparatus that are used, be it the rotary drum type, the sandwich type, the All-well apparatus or the /Moeller apparatus. It can be drawn out as tubes to follow the contour of the blood-carrying semipermeable membrane, or simply wrapped as sheets around the drums or laid end to end across the sandwich type model.

The same approach exists for applications such as hemoperfusion or peritoneal dialysis.

The intimate contact afforded between the blood and the sorbent matrix helps to quickly cleanse the blood of the toxic drugs. The procedure allows easy management of both multiple and single drug overdoes cases, since the matrix has the capacity of drawing out a wide variety of drugs. The encapsulation procedure offers a safe, economic and fast adjunct for the management of drug overdose patients.

What is claimed is:

1. A sorbent element for sorbing matter from a gaseous or liquid medium which matter can be substantially quantitatively desorbed from said element, said element consisting essentially of particulate sorbent material loosely encapsulated and confined within a rigid porous filter membrane having pore sizes less than the particle size of said sorbent, said element being of a substantially fixed, pre-determined volume such that the volume of the element is at least about 25% greater than the volume of said particulate sorbent both before and after sorption of matter by said sorbent, whereby said particulate sorbent agitates freely within said element both before and after its sorption of matter to facilitate the sorption and subsequent desorption of matter therefrom.

2. The sorbent element of claim 1 wherein said element has a volume of at least about 30% greater than that of the sorbent material.

3. The sorbent element of claim 1 wherein said sorbent material comprises charcoal.

4. The sorbent element of claim 3 wherein said filter-membrane material comprises polypropylene.

5. The sorbent element according to claim 1 wherein said rigid porous filter membrane comprises a rigid porous filter membrane material.

6. The sorbent element according to claim 1 wherein said rigid porous filter membrane comprises a porous filter membrane material and a rigid skeletal support structure over which said porous filter membrane material is contoured.

7. A process for removing solid matter from a liquid or gaseous medium, said process comprising:
   (a) providing a sorbent element consisting essentially of particulate sorbent material substantially loosely encapsulated and confined within a rigid porous filter membrane, having a pore size less than the particle size of said sorbent, said element being of a substantially fixed, pre-determined volume such that the volume of the element is at least about 25% greater than the volume of the particulate sorbent both before and after sorption of solid matter thereby, said particulate sorbent being capable of freely agitating within said element both before and after sorption;
   (b) admitting a liquid or gaseous medium containing solid matter and said sorbent element to a sealable vessel;
   (c) applying a substantially constant pressure to said medium and sorbent element within said vessel;
   (d) agitating the contents of said vessel, whereby said solid matter is sorbed by the particulate sorbent within said element;
   (e) removing said sorbent element from contact with said medium; and thereafter
   (f) removing the sorbed solid matter from said particulate sorbent while said sorbent remains within said element.

8. The process of claim 7 wherein said medium is a liquid.

9. The process of claim 8 wherein said medium is a biological sample and wherein said solid matter comprises drugs dissolved or dispersed within said sample.

10. The process of claim 7 wherein said medium is air.

11. The process of claim 7 wherein said sorbent comprises charcoal.

12. A sorbent element for the qualitative and quantitative analysis of solid matter dissolved or dispersed within a fluid, comprising a discrete integral capsule consisting essentially of a predetermined quantity of a particulate sorbent material for said solid matter substantially loosely encapsulated and confined within a rigid porous filter membrane, said sorbent element being of a substantially fixed predetermined volume such that the volume of said sorbent element both before and after sorption is at least about 25% greater than the volume of said sorbent material, whereby said sorbent material freely agitates within said element both before and after sorption of solid matter to facilitate the sorption and subsequent desorption of solid matter therefrom.

13. The sorbent element of claim 12 wherein said fluid is blood.

14. The sorbent element of claim 13 wherein said solid matter is one or more drugs.

* * * * *